United States Patent
Held et al.

(10) Patent No.: US 10,488,302 B2
(45) Date of Patent: Nov. 26, 2019

(54) DEVICE FOR CHECKING TYRES

(71) Applicant: PIRELLI TYRE S.P.A., Milan (IT)

(72) Inventors: Alessandro Held, Milan (IT); Vincenzo Boffa, Milan (IT); Daniele Pecoraro, Milan (IT); Valeriano Ballardini, Imola (IT)

(73) Assignee: PIRELLI TYRE S.P.A., Milan (IT)

( * ) Notice: Subject to any disclaimer, the term of this patent is extended or adjusted under 35 U.S.C. 154(b) by 0 days.

(21) Appl. No.: 16/066,264

(22) PCT Filed: Dec. 28, 2016

(86) PCT No.: PCT/IB2016/058038
§ 371 (c)(1),
(2) Date: Jun. 26, 2018

(87) PCT Pub. No.: WO2017/115290
PCT Pub. Date: Jul. 6, 2017

(65) Prior Publication Data
US 2019/0017902 A1    Jan. 17, 2019

(30) Foreign Application Priority Data
Dec. 28, 2015    (IT) .............................. UB2015A9454

(51) Int. Cl.
*G01B 11/24*    (2006.01)
*G01M 17/02*    (2006.01)
*G01N 21/88*    (2006.01)

(52) U.S. Cl.
CPC ........... *G01M 17/027* (2013.01); *G01B 11/24* (2013.01); *G01N 21/8806* (2013.01); *G01N 2021/8845* (2013.01)

(58) Field of Classification Search
CPC .. G01M 17/027; G01B 11/24; G01N 21/8806
See application file for complete search history.

(56) References Cited

U.S. PATENT DOCUMENTS

| 6,327,374 | B1 | 12/2001 | Piironen et al. | |
| 6,840,097 | B1 * | 1/2005 | Huber | G01B 11/30 356/237.1 |
| 7,187,437 | B2 * | 3/2007 | Shaw | G01B 11/162 356/237.2 |

(Continued)

FOREIGN PATENT DOCUMENTS

| DE | 4231578 A1 | 3/1994 |
| EP | 1030173 A1 | 8/2000 |

(Continued)

OTHER PUBLICATIONS

International Search Report and Written Opinion for International Application No. PCT/IB2016/058038, filed Dec. 28, 2016 on behalf of Pirelli Tyre S.P.A. dated May 11, 2017. 11 pages.

(Continued)

*Primary Examiner* — Maurice C Smith
(74) *Attorney, Agent, or Firm* — Steinfl + Bruno, LLP

(57) ABSTRACT

A device for checking a tyre in a tyre production line. The device includes a detection system, an illumination arrangement and a reflective element. The detection system includes a camera having a target line lying on an optical plane passing through the camera. The illumination arrangement includes first, second and third light sources, the second and third light sources being arranged at opposite sides with respect to the optical plane and symmetrically with respect to the first light source. The reflective element defines a reflective plane arranged perpendicular to the optical plane and arranged between the second and the third light source.

38 Claims, 6 Drawing Sheets

(56) References Cited

U.S. PATENT DOCUMENTS

| | | | | |
|---|---|---|---|---|
| 7,421,108 | B2* | 9/2008 | Kaneko | G01B 11/24 |
| | | | | 382/141 |
| 7,466,430 | B2* | 12/2008 | Braghiroli | G01M 1/02 |
| | | | | 356/601 |
| 9,175,952 | B2* | 11/2015 | Mizutani | G01B 11/24 |
| 2011/0018999 | A1 | 1/2011 | Joly et al. | |
| 2011/0288814 | A1* | 11/2011 | Mizutani | G01B 11/2522 |
| | | | | 702/150 |
| 2012/0134656 | A1 | 5/2012 | Mizukusa et al. | |
| 2014/0373614 | A1* | 12/2014 | Steinbichler | G01M 17/027 |
| | | | | 73/146 |

FOREIGN PATENT DOCUMENTS

| | | |
|---|---|---|
| EP | 1120640 A1 | 8/2001 |
| EP | 2078955 A1 | 7/2009 |
| EP | 2322899 A1 | 5/2011 |
| WO | 2015/004587 A1 | 1/2015 |
| WO | 2015/079370 A1 | 6/2015 |

OTHER PUBLICATIONS

International Search Report and Written Opinion for International Application No. PCT/IB2016/057712, filed Mar. 30, 2017 on behalf of Pirelli Tyre S.P.A. dated Mar. 30, 2017. 14 pages.
International Search Report and Written Opinion for International Application No. PCT/IB2016/058036, filed Dec. 28, 2016 on behalf of Pirelli Tyre S.P.A. dated Jul. 21, 2017. 12 pages.
International Search Report and Written Opinion for International Application No. PCT/IB2016/058052, filed Dec. 28, 2016 on behalf of Pirelli Tyre S.P.A. dated Jul. 16, 2017. 13 pages.

* cited by examiner

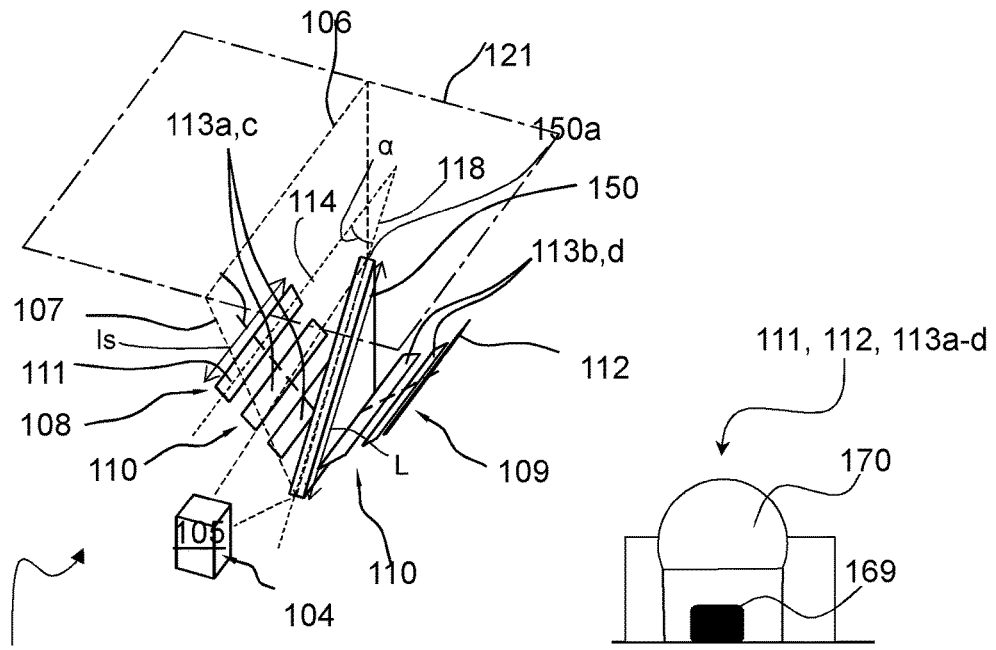
FIG. 6
FIG. 8
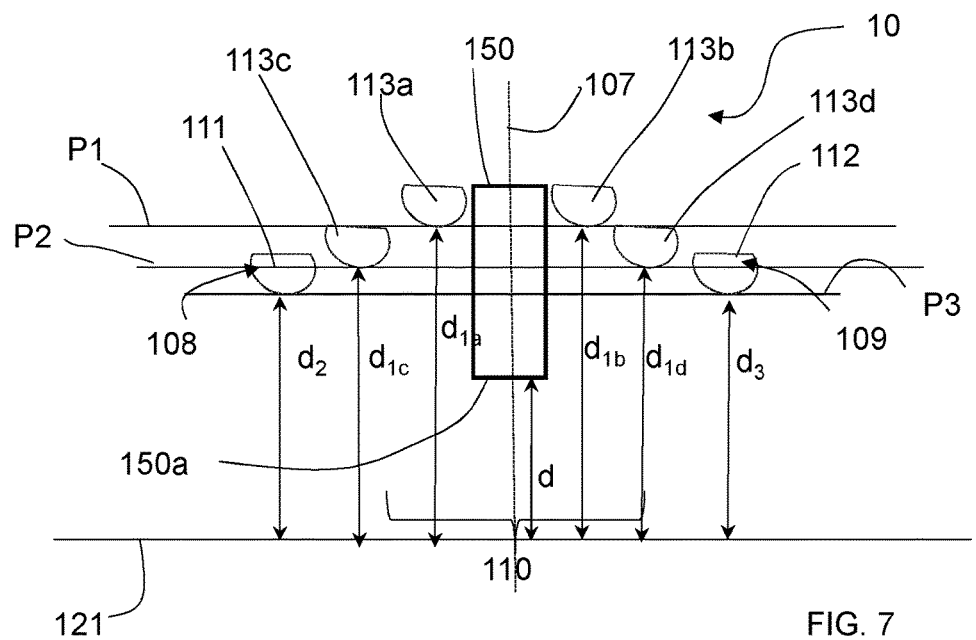
FIG. 7

DEVICE FOR CHECKING TYRES

CROSS REFERENCE TO RELATED APPLICATIONS

The present application is the U.S. National Stage of International Patent Application No. PCT/IB2016/058038 filed on Dec. 28, 2016 which, in turn, claims priority to Italian Application No. UB2015A009454 filed on Dec. 28, 2015.

The present invention concerns a device for checking tyres, for example in a tyre production line, in particular a device for checking for the possible presence of defects on, or close to, the surface of a tyre, more specifically on, or close to, the surface of the outer walls of a tyre.

Typically, a tyre has a substantially toroidal structure about a rotation axis thereof during operation, and has an axial mid-plane perpendicular to the rotation axis, said plane typically being a plane of (substantial) geometric symmetry, (e.g. ignoring possible minor asymmetries, such as the tread pattern and/or the internal structure).

Two portions of the tyre are identified here: the crown and the outer walls. The crown comprises the tread band, the belt and the corresponding portion of carcass structure radially inside them.

The term "outer wall" is meant to indicate one of the two portions of the tyre facing one another and that extend radially on opposite sides of the crown up to the beads, i.e. up to the two radially inner end edges of the tyre, having circular extension substantially perpendicular to the rotation axis; said beads being intended to each couple with a respective mounting rim. Each outer wall thus comprises a corresponding portion of carcass structure and, in a position axially outside of it, a portion made of suitable elastomeric material, generally called 'sidewall'.

Typically, the carcass structure comprises at least one carcass ply having respectively opposite end edges engaged with respective annular reinforcing structures, generally called "bead cores", integrated in the areas identified above with the name beads. In "tubeless" tyres, the carcass ply is entirely coated with a layer of elastomeric material preferably butyl-based, usually called "liner" having excellent characteristics of impermeability to air and extending from one bead to another.

The structure of an outer wall is also meant to entirely include the so-called "shoulder", i.e. the portion of the tyre for joining between the crown and the radially inner portion of the outer wall (in other words, the two shoulders correspond to the two radially and axially outer circular 'edges' of the tyre). The shoulder has circular extension substantially perpendicular to the rotation axis.

The term "tyre" is meant to indicate the finished tyre, i.e. after the moulding and vulcanization steps following the building step. Alternatively, the term "tyre" is meant to indicate a green tyre, i.e. before its vulcanization.

The term "component" of the tyre is meant to indicate any element that performs a function, or a portion thereof.

The terms outer or inner surface of the tyre, are respectively meant to indicate the surface that remains visible after the coupling of the tyre with its mounting rim and that which is no longer visible after said coupling.

The terms "optical", "light" and similar refer to an electromagnetic radiation used that has at least one portion of the spectrum falling within a widened range of the optical band, and not necessarily falling strictly within the optical band (in other words 400-700 nm), for example such a widened range of the optical band can extend from ultraviolet to infrared (for example wavelengths comprised between about 100 nm and about 1 µm).

In the present application a ray model of light radiation is adopted, i.e. it is presumed that light radiation incident on a point of a surface and generated by a non-pointed light source (in which case there would be a single ray) corresponds to a set of light rays incident on the point and having rectilinear propagation direction that connects each point of the light source with said point of the surface, where each of such rays has an associated fraction of the total light power incident on the point.

The term "directional light radiation" incident at a point of a surface is meant to indicate light radiation for which there is a solid angle having the point as vertex and amplitude less than or equal to $\pi/8$ steradians in which at least 75% of the total light power, preferably at least 90%, more preferably the entire light power falls.

The term "diffused light radiation" is meant to indicate a non-directional light radiation.

The term "grazing light radiation" incident at a point of a surface is meant to indicate a light radiation in which at least 75% of the total light power thereof incident on the point of the surface forms an angle of incidence less than or equal to 60° with a plane tangent to the surface at each said point.

The measurements expressed between light sources and/or sub-sources and a point belonging to an element outside of them are relative to the distance between a central point of said light sources and/or sub-sources and the aforementioned point.

The term "image" or synonymously "digital image" is meant to indicate in general a dataset, typically contained in a computer file, in which each coordinate (typically two-dimensional) of a finite set (typically two-dimensional and of the matrix type, i.e. N rows×M columns) of spatial coordinates (each typically corresponding to a pixel) is associated with a corresponding set of numeric values (which can be representative of magnitudes of a different type). For example, in monochromatic images (like those on the 'grayscale') such as set of values coincides with a single value in a finite scale (typically with 256 levels or tones), such a value for example being representative of the level of luminosity (or intensity) of the respective spatial coordinate when visualised, whereas in colour images the set of values represents the level of luminosity of multiple colours, or channels, typically the primary colours (for example in the RGB colour model red, green and blue, whereas in the CMYK colour model cyan, magenta, yellow and black). The term 'image' does not necessarily imply the actual visualisation thereof.

Every reference to a specific "digital image" (for example to a two-dimensional digital image initially acquired on the tyre) more generally covers any digital image that can be obtained through one or more digital processing operations of said specific digital image (like for example filtering, equalisation, "thresholding", morphological transformations—"opening", etc.,—gradient calculations, "smoothing", etc.).

The term "two-dimensional image" is meant to indicate a digital image each pixel of which has an associated piece of information representative of the reflectivity/diffusivity and/or of the colour of the surface, such as the images detected by common digital cameras.

The term "linear surface portion" is meant to indicate a surface portion having one dimension much larger than the other dimension perpendicular to it, typically greater by at least two orders of magnitude. The smaller dimension of the linear surface portion is typically smaller than or equal to 0.1 mm.

The term "linear image" is meant to indicate a digital image having a much greater number of columns of pixels than the number of rows, typically greater by at least two orders of magnitude. Typically, the number of rows is between 1 and 4 and the number of columns is more than 1000. The term "rows" and "columns" are used conventionally and are interchangeable.

The term "cycle time" within a production line comprising at least one work station, preferably a plurality of work stations, and inserted in a plant for producing tyres is meant to indicate, under normal operating conditions, the maximum transit time for a tyre being manufactured to pass through a work station in which at least one portion of a component of the tyre itself is built. For example, the cycle time can be comprised between about 20 and about 120 seconds.

In processes for producing and building tyres for vehicle wheels there is a need to carry out quality controls on the products made, with the purpose of avoiding tyres that are defective or in any case outside of the design specifications from being able to be released onto the market, and/or of progressively adjusting the apparatuses and machinery used, so as to improve and optimise the performance of the operations carried out in the production process.

Such quality controls include for example those carried out by human operators who spend a predetermined time period, for example comprised between 30 s and 60 s, carrying out a visual and tactile examination of the tyre; if, in light of his/her experience and sensitivity, the operator suspects that the tyre does not meet certain quality standards, the tyre itself is subjected to further checks, through a more detailed human check and/or suitable apparatuses, in order to more deeply evaluate possible structural and/or quality deficiencies.

US 2012/0134656 shows a lighting device and an inspection device of a tyre, which can easily detect anomalies in the shape of the tyre. A photographic portions photographs a portion of the inner surface of the tyre, whereas an actuator portion rotates the tyre and an inspection portion in a relative manner about an axis of the tyre, in a state of irradiation of light from a light source unit arranged along the inner surface of the tyre towards the circumferential direction of the tyre.

WO 2015/004587 to the same Applicant shows a method and relative apparatus, for checking tyres in a production line, comprising: providing a tyre to be checked; elastically deforming a portion of outer wall of the tyre through a compression force on an outer contact surface of the portion of outer wall, the compression force having an axial direction and going towards the plane of the middle line; illuminating an inner and/or outer surface of the portion of outer wall and detecting an image of the surface illuminated; generating a control signal representative of the image detected; and analysing the control signal in order to detect the possible presence of defects on the portion of outer wall.

EP 1120640 describes a method and an apparatus for checking the appearance and the shape of an object. First means for taking a photograph take a photo of a linear portion of an object illuminated by a first slit light to obtain data on the appearance, second means for taking a photograph take a photo of the same linear portion illuminated by a second slit light to obtain data on the shape, and the quality of the appearance and of the shape of the objects is judged based on the appearance data and the shape data.

In the field of tyre checks, the Applicant has set itself the problem of analysing the surface, inner and/or outer, of the tyre, through optical acquisition of digital images thereof and their subsequent processing, for example in order to detect the possible presence of defects visible on the surface. The defects sought can for example be irregularities on the surface of a tyre (unvulcanised compound, alterations in shape, etc.), structural unevenness, cuts, presence of foreign bodies on the surface, etc.

The Applicant has observed that in order for the check to be able to be used "on line" within a tyre production plant, it is necessary for the check itself to be carried out in short time periods and with low costs.

The Applicant has observed that in the "three-dimensional" images (i.e. each pixel of which is associated with information on the height of the surface, for example the images obtained with laser triangulation) some two-dimensional defects (i.e. that do not involve an alteration of the height of the surface, like for example cuts with matching edges) are difficult to detect, or actually undetectable, through image processing.

Moreover, the dimensional resolution of three-dimensional images, in particular in the height direction, is sometimes not sufficiently high as to detect defects that are not very pronounced.

The Applicant has therefore worked out that it is advantageous to detect and analyse "two-dimensional" images (in addition or as an alternative to 3D ones). Moreover, the Applicant has worked out that, in order to obtain digital images of portions of inner surface of the tyre, the provision of a reflective surface that reflects a target line is advantageous since it also makes it possible to visualise portions of inner surface otherwise difficult or impossible to visualise in the camera due to the limited space available to move the camera, which therefore cannot be positioned as desired. At least one reflective surface therefore directs an optical path of the light where desired, so that it can in any case reach the camera and for example a sensor positioned in it.

The Applicant has realised that in apparatuses for checking tyres with optical acquisition of two-dimensional images of the type described in US 2012/0134656, the arrangement of the light sources fixed to one end of a mirror of massive dimensions translates into a high overall bulk of the device that results in a relatively large minimum distance between light sources and surface of the tyre also in the case of maximum possible approach with the device to the inner surface of the tyre.

The Applicant has also realised that checking apparatuses with optical acquisition of two-dimensional images of the type described in EP 1120640, in which two images of an inner portion of tyre are acquired with a matrix image projection camera and a linear camera, include a structure and an arrangement of the light sources (see the arc 6 of light sources) that makes the total bulk of the light source group very high as well as preventing getting closer than a certain distance from the surface of the tyre.

The light emitted by the light sources has an optical path, including reflections on a mirror 8, that is relatively long before reaching the linear camera. Moreover, the provision of two cameras illuminating the same portion makes the apparatus very complex, bulky and not very versatile in acquiring images in diffused and/or grazing light.

The Applicant has also realised that the method and the apparatus for checking with optical acquisition of two-dimensional images of the type described in WO 2015/004587 are not optimised for the illumination necessary at the inner surface of the tyre, i.e. they do not describe light sources capable of generating an grazing and/or diffused illumination that the Applicant considers optimal for the illumination of surface portions of the tyre in order to detect defects thereof.

The Applicant has therefore set itself the problem of devising a device for checking tyres capable of acquiring two-dimensional images (in particular for detecting defects on the surface of tyres) of the surface of a tyre, which is suitable for insertion on-line inside a tyre production line of a production plant, in other words suitable for being used with reduced operating times and costs, and capable of providing reliable results. In particular, the Applicant has set itself the problem of devising a device capable of acquiring two-dimensional images in particular for the detection of defects on the inner surface of a tyre, where the "manoeuvring space" in which the device can be moved is very small and the illumination of some surface portions is particularly complex due to undercuts and convexities present in the inner surface of the tyre itself. This configuration of the inner surface of the tyre, added to the generally black colour thereof, also requires high illumination of the surface portion to be checked. This can be obtained through high-power light sources or by getting as close as possible with the light sources to the tyre itself.

The Applicant has perceived that being able to associate a camera, a reflective element and at least three light sources, exploiting the geometric arrangement of such elements it could be possible to acquire images both in diffused light and in grazing light at a closer distance particularly useful for the purposes of the aforementioned checking of the tyre.

More precisely, the Applicant has finally found that a device comprising a camera having a target line, at least three light sources and a reflective element, the first light source and the reflective element being arranged between the second light source and the third light source, is particularly compact and manoeuvrable, can be brought adequately close to the surface of the tyre and/or can be inserted inside the tyre itself.

Moreover, it proves particularly versatile in acquiring images with high-power diffused light and/or with wide solid angle of incidence and/or in acquiring images with grazing light from at least one or from both sides of the target line, also allowing the detection of three-dimensional defects from two-dimensional images. Furthermore, the device is capable of approaching to a relatively short distance from the inner surface of the tyre so as to illuminate it with an adequate light intensity to illuminate it correctly.

In accordance with a first aspect, the invention concerns a device for checking a tyre in a tyre production line.

Preferably, a detection system is provided comprising a camera having a target line lying on an optical plane passing through the camera.

Preferably, a first light source, a second light source and a third light source are provided, said second light source and said third light source being arranged at opposite sides with respect to said optical plane and symmetrically with respect to said first light source.

Preferably, said first light source is adapted for emitting a first diffused light radiation on said surface portion, and said second light source and third light source are adapted for emitting a second grazing light radiation and a third grazing light radiation on a surface portion of said tyre coinciding with or close to said target line.

Preferably, a reflective element is provided defining a reflective plane arranged perpendicular to said optical plane, said reflective element being arranged between said second light source and third light source, said reflective element being adapted for reflecting said target line by an angle comprised between about 60° and about 120° and wherein a minimum distance between said reflective plane and a focusing plane of said camera passing through said reflected target line is less than a minimum distance between one of said first light source, second light source and third light source and said focusing plane.

In accordance with a second aspect, the invention relates to a kit for checking a tyre.

Preferably, the kit comprises a device according to the first aspect.

Preferably, the kit comprises a deformation element configured to form an elastically deformed portion on said tyre through physical contact.

According to a third aspect, the invention relates to a tyre checking line.

Preferably, a support for a tyre is provided.

Preferably, a robotized arm is provided.

Preferably, a device according to the first aspect is provided coupled with said robotized arm.

The Applicant considers that for the purposes of checking the surface of tyres, in particular their inner surface, in order to detect possible defects on said surface, through acquisition and processing of two-dimensional digital optical images through a camera, the arrangement of at least three light sources, where the first light source is adapted for emitting diffused light on the portion of tyre to be checked and the second light source and the third light source are adapted for emitting grazing light radiation and lie, respectively, on opposite sides of the optical plane defined by the camera and the first light source is arranged between the second and the third light source, gives the possibility of illuminating the portion to be checked with two types of radiation—grazing and diffused. In this way, it is possible to highlight, in a subsequent analysis of the images obtained, defects that can for example be present in a portion of the inner surface of the tyre. Moreover, the interposition of a reflective element between the light sources makes it possible to visualise portions of tyre, in particular portions of the inner surface of the tyre, otherwise unable to be visualised, for the following reasons. A tyre has a diameter in general much greater than its width and therefore a device adapted for at least partially entering into a tyre and detecting defects thereof must preferably maintain a compactness in particular in the extension corresponding to the width of the tyre. Positioning the camera therefore "behind" the light sources so as to directly detect the light reflected by the illuminated surface would make the device unsuitable for examining some portions of the inner surface of the tyre, in particular relative to the inner surface axially opposite the sidewall and to the inner surface of the shoulder, since the extension given by camera and light sources one behind the others is generally too high. The presence of a reflective element allows a different positioning between light sources and camera so as to obtain a very compact device, in particular in one direction, so that the light reflected by the illuminated surface can be sent to the camera through the reflective surface taking a different direction with respect to the "direct" one. Furthermore, fixing the angle of reflection of the target line within the range 60°-120° is advantageous since it allows a relative arrangement between light sources, reflective element and camera that maximises the compactness of the device.

The Applicant also considers that it is preferable to be able to approach to a relatively short distance from the inner surface of the tyre so as to illuminate it with a high light intensity, without using light sources of a power such as to cause a high dispersion of heat. The Applicant also considers that, since the presence of different light sources is desired to have different types of illumination, grazing and diffused, optimal for detecting defects, as well as to have a high light intensity in the surface portion to be illuminated, this aspect also involves a relative "widening" of the dimensions of the device in the direction, at the side of the optical plane, in which all of these light sources are positioned. The Applicant therefore considers that providing a reflective element that is the "closest" element in the device to the surface to be checked, keeping the light sources further away, allows a minimisation of the distance of the optical path of the light emitted by the light sources, reflected by the surface portion of the tyre and detected by the camera, therefore exploiting the entire light intensity produced by the light sources, at the same time minimising the risks of contact, with consequent damage, between device and tyre.

The present invention, in one or more of the aforementioned aspects, can also have one or more of the preferred characteristics described hereinafter.

Preferably, said camera is a linear camera and said surface portion is a linear surface portion.

Preferably, said minimum distance between said reflective plane and said focusing plane of said camera passing through said reflected target line is less than each minimum distance between said first light source, second light source and third light source and said focusing plane.

In other words, the reflective plane is the closest element to the focusing plane with respect to all of the light sources.

Preferably, said first light source includes a first sub-source and a second sub-source, said first sub-source and said second sub-source being arranged symmetrically with respect to said optical plane. More preferably, said first light source includes a third sub-source and a fourth sub-source, said third sub-source and said fourth sub-source being arranged symmetrically with respect to said optical plane. Even more preferably, the first sub-source and the second sub-source are arranged symmetrically at the sides of said reflective element. Even more preferably, the third sub-source and the fourth sub-source are arranged symmetrically at the sides of said reflective element.

The first light source is responsible for the diffused illumination of the surface portion.

Theoretically, the greatest possible number of such diffused light sources is desired to obtain an optimal illumination. However, this would clash with the requirement of compactness of the device, desired since for example it is preferred for it to be able to be inserted inside the tyre. The provision of two, and more preferably four, sub-sources according to the Applicant is the optimal compromise between number of diffused light sources and final size of the device.

Moreover, the symmetry of the light sources with respect to the optical plane is preferred and is preferably maintained also by the arrangement of the first light source that preferably includes two or four sub-sources positioned at the two sides of the optical plane. The symmetry of the light sources allows an illumination of the surface portion of the tyre that is substantially symmetrical and therefore images with distinct illumination are more easily compared with each other, simplifying the processing algorithms of the images detected by the camera.

Preferably, said second light source and said third light source each comprise a single sub-source. In this way, they produce a respective preferably grazing directional radiation.

Preferably, said first sub-source and said second sub-source of said first light source are coplanar and define a plane substantially parallel to the focusing plane. More preferably, a distance between said focusing plane and a plane passing through said first sub-source and said second sub-source is comprised between about 85 mm and about 95 mm.

Preferably, said third sub-source and said fourth sub-source are coplanar and define a plane substantially parallel to the focusing plane. More preferably, a distance between said focusing plane and a plane passing through said third sub-source and said fourth sub-source is comprised between about 75 mm and about 85 mm.

Preferably, said second light source and said third light source are coplanar and define a plane substantially parallel to the focusing plane. More preferably, a distance between a plane parallel to said focusing plane and passing through a sub-source of said first light source and a plane parallel to said focusing plane and passing through said second light source and said third light source is comprised between about 10 mm and about 40 mm.

Since the reflective element, in order to reflect the optical path of the light radiation, is at a certain angle with respect to the light sources, there is a minimum size of the device in two directions perpendicular to one another and coplanar to the optical plane, due to the aforementioned angle. Therefore, arranging the light sources in different planes offset from one another and at the preferred distances indicated does not increase the size of the device, since they are "comprised within" the dimensions in two perpendicular directions given by the angle of the reflective element. The Applicant considers that arrangement in offset planes is the optimal arrangement for correctly illuminating the surface portion of the tyre with grazing and diffused light.

Preferably, a distance between said first light source and said focusing plane is greater than a distance between said second light source and said focusing plane or between said third light source and said focusing plane.

The first light source is preferably substantially further from the surface to be illuminated precisely to obtain in the optimal manner a diffused light having a high intensity, whereas the second light source and the third light source generating the grazing light are positioned closer and correctly angled.

Preferably, at least one of said sub-sources of said first light source or of said second light source or of said third light source defines a main direction of extension substantially parallel to said optical plane.

More preferably, all of the sub-sources of said first light source, of said second light source and of said third light source define a main direction of extension substantially parallel to said optical plane.

The main direction of extension preferably coincides with an axis of the light source in its direction of greatest extension.

"Substantially parallel" referring to the arrangement of two light sources and in particular their respective main directions of extension comprises all of the configurations in which two distinct light sources have respective main directions forming an angle the size of which in radians substantially coincides with the sine and tangent value thereof. This occurs for angles having a value less than 5°.

The Applicant considers that in order to check the surface of tyres in a production line, in particular in order to detect possible defects on said surface, through acquisition and processing of two-dimensional digital optical images, the arrangement of at least three light sources with a respective main direction of extension substantially parallel to the optical plane in which the target line of the camera lays, where the second light source and the third light source respectively lay on opposite sides of the optical plane and the first light source is arranged between the second and the third, gives particular compactness and manoeuvrability to the apparatus, and/or allows a diffused illumination of the target line with a wide solid angle and/or allows images to be acquired both in diffused light and in grazing light from one or both sides of the target line.

Preferably, said reflective plane defines a main direction of extension substantially parallel to said optical plane.

The main direction of extension preferably coincides with an axis of the reflective plane in its direction of greatest extension.

This configuration increases the compactness of the device. Advantageously, the reflective plane can be substantially rectangular, and the main direction of extension is that defined by a longer side of the rectangle.

Preferably, said main direction of said reflective plane forms an angle with said main direction of said first light source, or of said second light source, or of said third light source, comprised between about 30° and about 60°.

This angle is preferred to make it possible both to use the reflective plane to reflect the target line in the desired manner, and to keep the compactness of the device.

Preferably, along said main direction of extension said first sub-source, said second sub-source, said third sub-source, or said fourth sub-source of said first light source, or said second light source, or said third light source or said reflective plane have a substantially rectilinear configuration.

In this way, making the same light source or the reflective plane having such linear or rectilinear extension is simplified and increases the compactness.

Preferably, a length along the main direction of extension of said reflective plane is greater than a length along said main direction of extension of said first sub-source, of said second sub-source, of said third sub-source, or of said fourth sub-source of said first light source or of said second light source or of said third light source.

The fact that said reflective element is angled with respect to the light sources makes it possible to have a greater length of the reflective plane without invalidating the maximum size of the device, since the angle compensates for the great length.

Preferably, the length of one among said first sub-source, second sub-source, third sub-source and fourth sub-source of said first light source and of said second light source, or the length of one among said first sub-source, second sub-source, third sub-source and fourth sub-source of said first light source and of said third light source, is substantially the same.

In this way, the system is very compact and the maximum size in one direction is given by the maximum size in the main direction of a light source.

Preferably, said second light source and said third light source are arranged symmetrically with respect to said optical plane.

A symmetry in the light sources, which are arranged at the two sides of the optical plane of the detection system, allows an easier comparison of images obtained with the different types of illumination obtained by illuminating the second surface portion with the second light radiation or the third light radiation.

Preferably, said respective light sources or sub-sources have a size along the main direction of extension at least double, more preferably at least one order of magnitude greater than, the size perpendicular to said main direction of extension.

Preferably, each of said light sources or sub-sources has the size along said main direction of extension less than or equal to 15 cm.

Preferably, each of said light sources or sub-sources has the size along said main direction of extension greater than or equal to 5 cm.

Preferably, each of said light sources or sub-sources has the size perpendicular to said main direction of extension less than or equal to 3 cm, more preferably greater than or equal to 2 cm. The aforementioned dimensions allow the sub-sources to be effectively shaped to the target line and to reduce bulk.

Preferably, said respective light sources or sub-sources are structurally and/or dimensionally the same as each other. In this way, the light source group is simplified in structure, operation and maintenance.

Preferably, a first axial end along said main direction of said second light source, a first axial end along said main direction of said third light source and a first axial end of one among said first sub-source, second sub-source, third sub-source and fourth sub-source of said first light source are coplanar.

More preferably, a second axial end along said main direction of said second light source, a second axial end along said main direction of said third light source and a second axial end of one among said first sub-source, second sub-source, third sub-source and fourth sub-source of said first light source are coplanar.

Along the main direction therefore, the size of the device is substantially given by the dimension of the light sources that is limited between two substantially parallel planes on which the opposite axial ends of the light sources rest. From these two parallel planes between which the light sources are confined, the reflective plane can project since it represents the closest element to the focusing plane.

Preferably, a drive and control unit is provided configured to selectively activate at least one among said first light source, second light source and third light source.

Preferably, a drive and control unit is provided configured to activate said camera to acquire a respective two-dimensional image of said surface portion in synchrony with the activation of said at least one among said first light source, second light source and third light source.

The drive and control unit preferably drives both one or more light sources and the camera so as to obtain, for a surface portion to be examined of the tyre, preferably for an inner surface portion, one or more images, preferably two-dimensional, of the portion itself. For each surface portion, in which the illumination takes place through the first light source, the radiation coming from said first light source is preferably emitted at a certain frequency to limit the power emitted by the aforementioned first light source and thus also the amount of heat dissipated. The image of the illuminated portion is acquired at the illumination thereof, i.e. when the first light source emits radiation. For this purpose, a time synchrony is therefore obtained between the switching on of the first light source and the acquisitions of the first images. The same preferably occurs at the activation of the second light source or of the third light source, which emit an grazing radiation on the surface portion.

The switching on of each light source therefore preferably takes place at a distinct time from that at which the switching on of the other light sources takes place. In other words, in each time interval, only one among the first light source, the second light source or the third light source is switched on. In the case of the sub-sources of the first light source, they switch on and off in unison, i.e. they are synchronised with each other in switching on and off.

The possibility of having preferably at least two distinct images for each portion obtained by illuminating the portion alternately with the first light source, with the second light source or with the third light source allows a comparison of different images of the same surface portion in different illumination conditions (diffused and grazing) in order to detect the defects thereof.

Preferably, said drive and control unit is adapted for driving said detection system so as to acquire three distinct images, each image corresponding to the switching on of a different light source among said first light source, said second light source and said third light source.

Obtaining three images in different illumination conditions, diffused central illumination, and grazing from the two opposite half-spaces to the optical plane, allows processing of the three images that is optimal for detecting defects.

Preferably, it is foreseen to process said first image or second image or third image, so as to detect possible defects in said first surface portion or second surface portion or third surface portion of said tyre.

Preferably, said reflective element is adapted for reflecting said target line by an angle of about 90°. In this solution, the best geometric arrangement of the device is reached, again with regard to compactness, also preferably entailing an angle of the reflective element of 45° with respect to the focusing plane.

Preferably, the reflective element includes a reflective layer defining said reflective plane, said reflective layer being an outermost layer of said reflective element on which an optical path of a light radiation directed to said camera reflects.

Advantageously, there are no further reflections and therefore elongations of the optical path of the radiation incident on the reflective plane if the reflective layer is the first, outermost, layer on which the radiation coming from the tyre hits directly.

Preferably, a first support is provided to which said camera is fixed.

Preferably, said drive and control unit is fixed to said first support.

Given the preferred high frequency at which the light sources are alternately activated, the Applicant considers that delays in the control signals can be minimised by positioning the drive and control unit substantially "close" to light sources and camera.

Preferably, a second support is provided to which said first light source, said second light source and said third light source and said reflective element are fixed.

More preferably, said first support and said second support are connected and made to form a unit by a connecting arm. The device is substantially a single element that is inserted preferably inside the tyre. Therefore, the various elements of the device, i.e. light sources, camera and reflective element, form a unit with one another.

More preferably, said second support comprises two equidistant plates between which said first light source, said second light source and said third light source are arranged. In this way, the light sources form a single unit.

Preferably, said first light source, or said second light source or said third light source are fixed to said second support through a thermo-conductive paste.

Preferably, said first support or said second support is made at least partially from aluminium.

Preferably, said first support or said second support comprises a heat dispersion fin arrangement.

Considering that in a tyre, in order to detect defects on the surface, there is often the need to illuminate shaded or undercut surface portions and in any case that are often black in colour, the light sources need to generate a large amount of light that entails a negative side effect—the generation of heat with relative high temperatures. For this reason, preferably at least one light source and preferably all of the light sources, include a support. Advantageously, each support is made of aluminium due to its lightness and heat conductivity, and preferably includes a finned arrangement for cooling. Furthermore, in order to maximise the heat transfer, a thermo-conductive paste, typically used in chips, is also used to obtain an area with large heat exchange surface between any two contact surfaces in the device.

Preferably, said first light source or said second light source or said third light source includes one or more light emitting diodes (LEDs). More preferably, said first light source or said second light source or said third light source include a number of diodes greater than or equal to 6.

The LEDs ensure a high efficiency and therefore a relative energy saving with respect to other light radiation sources, and such high efficiency is also advantageous due to the low generation of heat.

Advantageously, the LEDs also have a long operating time: they are less delicate and in any case the light sources used preferably do not include a single LED but a plurality of LEDs, and therefore malfunctions of one or more of the LED is permitted, which is not possible with different types of light radiation sources. The LEDs finally advantageously ensure quick switching on and off.

Preferably, said first light source or said second light source or said third light source includes a converging lens adapted for narrowing an emission field angle of said first light radiation or of said second light radiation or of said third light radiation to a value comprised between about 15° and about 45°.

More preferably, each of said first light source, said second light source and said third light source includes a converging lens adapted for narrowing an emission field angle of said first light radiation, of said second light radiation and of said third light radiation to a value comprised between about 15° and about 25°.

The choice of the light emission angle by the light source influences the result of the final light intensity. For the same effective intensity of the LED, the greater than emission angle the better the radiation emitted on the surface portion is distributed, but on the other hand the worse the light intensity.

Since the light sources are relatively close to the surface portions to be examined and illuminated, the Applicant considers it advantageous to use one (or more) lenses suitably designed with the purpose of concentrating the beam of light radiation so as to considerably increase the light intensity thereof in the surface portion to be illuminated. An emission angle comprised between about 15° and about 25° allows an optimal compromise between a uniform radiation and a sufficient intensity in the surface portion of tyre to be illuminated.

Preferably, a respective angle formed between said focusing plane and any plane passing through said target line and any point respectively of said second light source or third light source is less than or equal to 60°. In this way a wide solid angle of the diffused light is obtained.

Preferably, said surface portion belongs to a surface portion of a shoulder of said tyre.

Preferably, said surface portion corresponds inside the tyre to a surface portion of a sidewall of said tyre.

Preferably, said surface portion belongs to a bead surface portion of said tyre.

Due to the characteristics of compactness and illumination, the device of the invention is advantageously used inside the tyre to detect defects in the inner surface thereof.

Preferably, said deformation element is adapted for applying a deformation to said tyre as a function of a type of tyre to be checked.

Not all tyres have the same characteristics of size and flexibility. Therefore, the force applied by the deformation element is preferably correlated to the type, and therefore to the characteristics, of the tyre to be checked.

Advantageously, said deformed surface includes at least in part said surface portion.

The deformation of a surface portion of the tyre highlights defects, like for example cuts, which are generally not visible otherwise. It is thus preferred for an illumination of a surface portion that is also deformed, i.e. forms part of the surface to be checked, to be carried out.

Preferably, the distance between said first light source and said surface deformed by said deformation element is comprised between about 85 mm and about 95 mm.

Preferably, the production line includes a rotation system adapted for setting said tyre and said robotized arm in relative rotation with respect to one another so as to modify an angular position of said surface portion of said tyre with respect to said robotized arm. More preferably, said tyre is set in rotation with respect to said robotized arm.

The relative rotation between tyre and robotized arm allows 360° checking of the tyre itself. Advantageously, the tyre is rotated, instead of the detection system, since the first operation is simpler: the rotation of the detection system could result in it being damaged or inaccurate acquisition of the images due to vibrations induced by continuous movement.

Advantageously, the production line includes a deformation element configured to apply a force to a surface to be checked of said tyre.

Preferably, said drive and control unit is configured to drive said detection system to acquire a plurality of images of said surface portion at predetermined time intervals during a rotation of 360° of said tyre carried out by said rotation system.

In this way, the tyre is checked in its entirety.

Advantageously, said deformation element is adapted for generating an elastic deformation on a surface forming part of an outer shoulder or of a sidewall of said tyre.

The Applicant has found that the defects most highlighted through compression are generally present at the outer shoulder or the sidewall of the tyre, and in the corresponding deformed inner surface portion, and therefore advantageously the pressing or thrusting by the deformation element is exerted in one or both of these areas.

Further characteristics and advantages will become clearer from the detailed description of some example but not exclusive embodiments of a device and of a kit for checking a tyre in a tyre production line, in accordance with the present invention.

Such a description will be outlined hereinafter with reference to the attached figures, provided only for indicating purposes, and therefore not limiting, in which:

FIG. 6 shows a partial and schematic perspective view in simplified form of a detail of the device of FIG. 1;

FIG. 7 shows a partial and schematic side view in simplified form of a detail of the device of FIG. 1;

FIG. 8 shows a side view, in section and schematic, of a detail of the device of FIG. 1.

Figure 1:
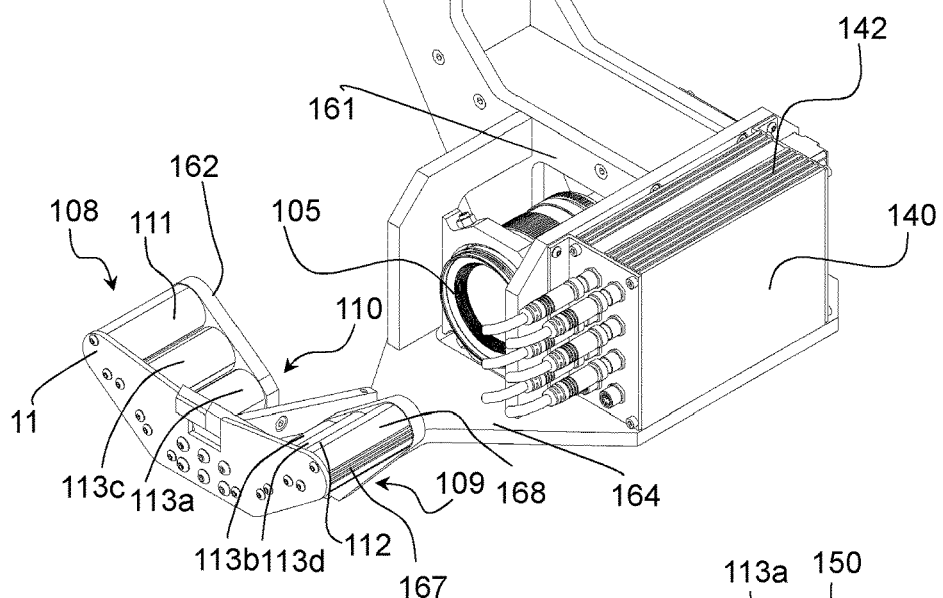
FIG. 1 shows a front perspective view of a device for checking a tyre according to the present invention.

With reference to the figures, reference numeral 10 generally indicates a device for checking a tyre 200 in accordance with the present invention.

Figure 5:
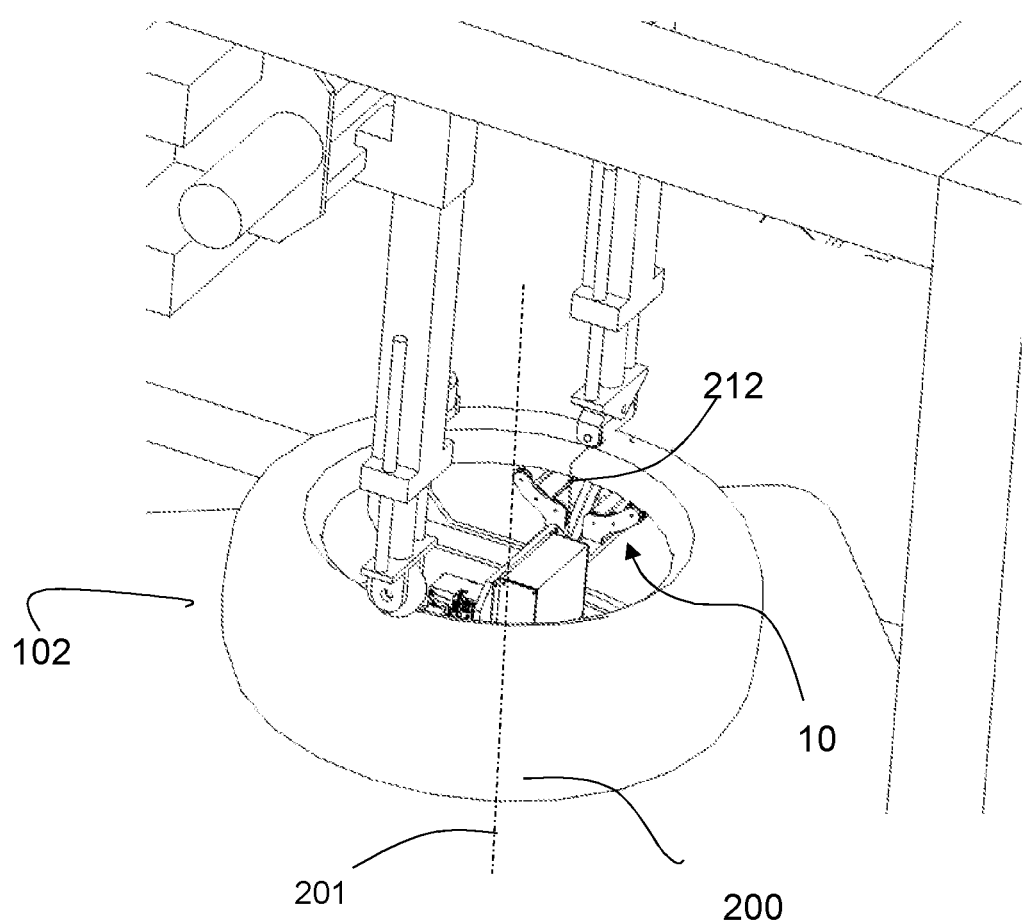
FIG. 5 shows a partial and schematic perspective view of a device for checking a tyre in accordance with a first embodiment of the present invention.

With particular reference to FIG. 5, a support 102 is adapted for supporting the tyre 200 on a sidewall and for rotating it about its rotation axis 201, typically arranged according to the vertical. The support 102 is typically actuated by a movement member not described and illustrated any further, since it can for example be of the known type. The support 102 for the tyre can possibly be configured to lock it, for example the respective supported bead.

Figure 9:
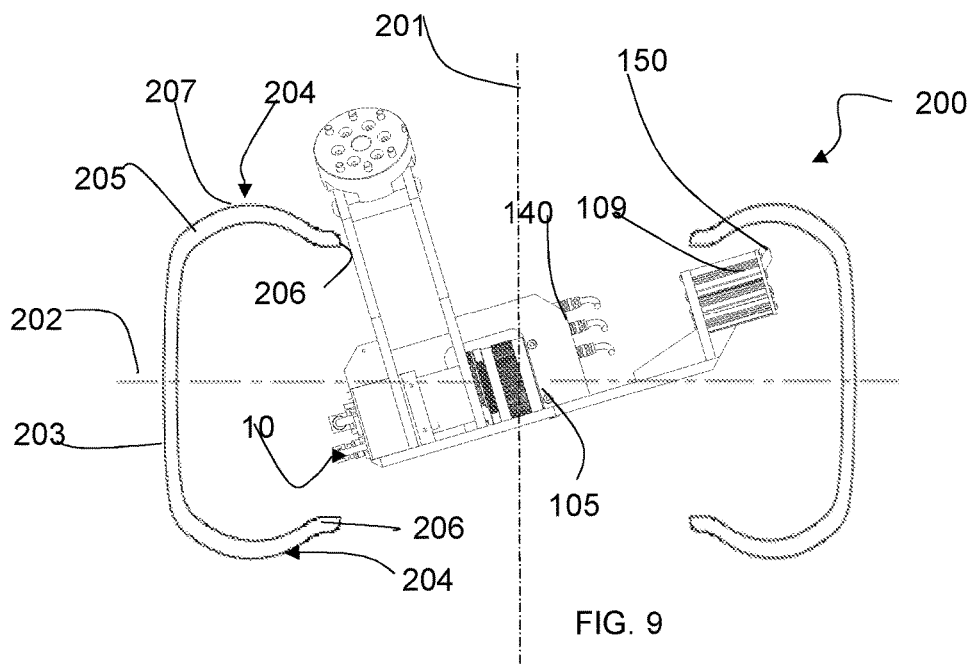
FIGS. 9 to 12 show a perspective view, partial and schematic, of a kit for checking a tyre in different operative steps.

The tyre 200 has a substantially toroidal structure about the rotation axis 201, and has an axial mid-plane 202 (represented in section by a broken straight line in FIGS. 9, 10, 11 and 12) perpendicular to the rotation axis 201. The tyre is made up of a crown 203 and outer walls 204. In turn, the latter are each made up of a shoulder area 205, a bead area 206 and a radially central area or sidewall 207 arranged between shoulder and bead, as can be seen in FIGS. 9 and 11.

With reference now to FIGS. 6 and 7, the device 10 is represented in simplified form to clearly indicate the functional parts thereof. Preferably, the device 10 comprises a detection system 104 comprising a camera 105, preferably of the linear type, having a target line 106 lying on an optical plane 107 passing through the aforementioned camera 105. Moreover, the camera 105 defines a focal plane 121 in which a portion to be illuminated of tyre surface is focuses on. Preferably, the optical plane 107 and the focal plane 121 are perpendicular to one another (see for example FIG. 6 or 7).

The device 10 also comprises a first light source 110, a second light source 108 and a third light source 109 adapted for respectively emitting a first light radiation, a second light radiation and a third light radiation to illuminate a surface portion 212, also preferably linear (visible in FIG. 5), of said tyre 200 coincident with the target line 106 (for example when the surface portion is planar) or close to the target line 106 (due to the curvilinear shape of the surface of the tyre).

The detection system 104 is adapted for acquiring a respective two-dimensional digital image of the linear surface portion 212 illuminated by at least one among the first light source, the second light source and the third light source.

The first light radiation emitted by the first light source 110 is diffused on the linear surface portion 212 of the tyre 200, whereas the second light radiation and the third light radiation emitted, respectively, by the second light source 108 and by the third light source 109 are grazing on the surface portion 212 of the tyre 200.

The detection system, through the camera 105, is adapted for acquiring a respective two-dimensional digital image of the linear surface portion 212 illuminated by at least one among the first light source 110, the second light source 108 and the third light source 109.

Preferably, the second light source 108 and the third light source 109 each comprise at least one respective sub-source. Even more preferably the second light source 108 and the third light source 109 each comprise a single respective sub-source 111, 112, the two sub-sources being positioned symmetrically with respect to the optical plane 107. Preferably, the two sub-sources 111 and 112 respectively lie at the opposite sides with respect to the optical plane 107 and are equidistant from it.

Preferably, the sub-sources 111, 112, of the second light source 108 and of the third light source 109, respectively, are the same distance $d_2$ and $d_3$ from the focusing plane 121 (i.e. $d_2=d_3$). Therefore, a plane P3 that joins the two sub-sources 111 and 112, is substantially parallel to the focusing plane 121 of the linear camera 105 and is preferably distant from it by a value comprised between about 55 mm and about 65 mm. The plane P3 and its distance from the focusing plane 121 called $d_2$ (which as stated is equal to $d_3$) is schematically represented in FIG. 7.

Preferably, the first light source 110 consists of four sub-sources, a first sub-source 113a, a second sub-source 113b, a third sub-source 113c and a fourth sub-source 113d, respectively, distributed in pairs on both sides of the optical plane 107 and symmetrically with respect to such a plane. More specifically, the first sub-source 113a and the second sub-source 113b of the first light source 110 are arranged symmetrically with respect to the optical plane 107 and are more preferably equidistant from it, and the third sub-source 111c and the fourth sub-source 111d are arranged symmetrically with respect to the optical plane 107 and more preferably are equidistant from it.

Preferably, the first sub-source 113a and the second sub-source 113b of the first light source 110 are the same distance $d_{1a}$ and $d_{1b}$ from the focusing plane 121 (i.e. $d_{1b}=d_{1a}$). Therefore, the two sub-sources are joined by a plane, called P1 (again see FIG. 7), substantially parallel to the focusing plane 121 of the linear camera 105 and distant from it by a value $d_{1a}$ comprised between about 85 mm and about 95 mm.

Similarly, the third sub-source 113c and the fourth sub-source 113d of the first light source 110 are the same distance $d_{1c}$ and $d_{1d}$ from the focusing plane 121 (i.e. $d_{1c}=d_{1d}$). Therefore, the two sub-sources 113c and 113d are joined by a plane P2, substantially parallel to the focusing plane 121 of the linear camera 105 and distant from it by a value comprised between about 75 mm and about 85 mm.

Preferably, the distance $d_{1a}=d_{1b}$ between the first sub-source 113a and the focusing plane 121 and between the second sub-source 113b and the focusing plane 121 of the linear camera 105 is greater than the distance $d_2$ between the second light source 108 and the focusing plane 121 or than the distance $d_3$ between the third light source and the focusing plane 121. More preferably, the distance $d_{1c}=d_{1d}$ between the third sub-source 113c and the focusing plane 121 or between the fourth sub-source 113d and the focusing plane 121 is intermediate between the distance of the first sub-source 113a and the second sub-source 113b and the focusing plane 121 and the distance of the second light source 108 and of the third light source 109 and the focusing plane 121. As a result the first diffused light source 110 is further from the linear surface portion 212 of the tyre 200 to be illuminated with respect to the second light source 108 and to the third light source 109, the second light source 108 and the third light source 109 generating grazing light are thus positioned closer to the aforementioned linear surface portion 212. In this way, it is possible to obtain an grazing light with a correct geometry of the device 10.

Each sub-source 111, 112, 113a-d has a respective main direction of extension (broken line 114 in FIG. 6) that preferably extends substantially parallel to the optical plane 107 and thus to the target line 106. Therefore, all of the light sources or the sub-sources are preferably parallel to one another, i.e. aligned, along their dimension of greater extension.

Preferably, the sub-sources 111, 112, 113a-d have a dimension along the main direction of extension 114 comprised between about 5 cm and about 15 cm and a dimension along the direction perpendicular to the main direction of extension 114 comprised between about 2 cm and about 3 cm.

As an example, the sub-sources 111, 112, 113a-d have a dimension along the main direction of extension 114 equal to about 6 cm and a dimension along the direction perpendicular to the main direction of extension 114 equal to about 2.5 cm.

Each sub-source 111, 112, 113a-d typically comprises a plurality of LED sources 169 arranged aligned along the main direction of extension 114. Preferably, each sub-source 111, 112, 113a-d comprises, positioned above each LED source 169, a converging lens 170, adapted for converging by about 30° the light beam emitted by the LED source 169, as represented in FIG. 8. The light beam emitted by each LED source 169 is therefore restricted preferably to an angle comprised between about 20° and about 40°.

A representation of an example embodiment of the device represented in a simplified manner in FIGS. 6-8 is given in FIGS. 1 to 4.

Figure 2:
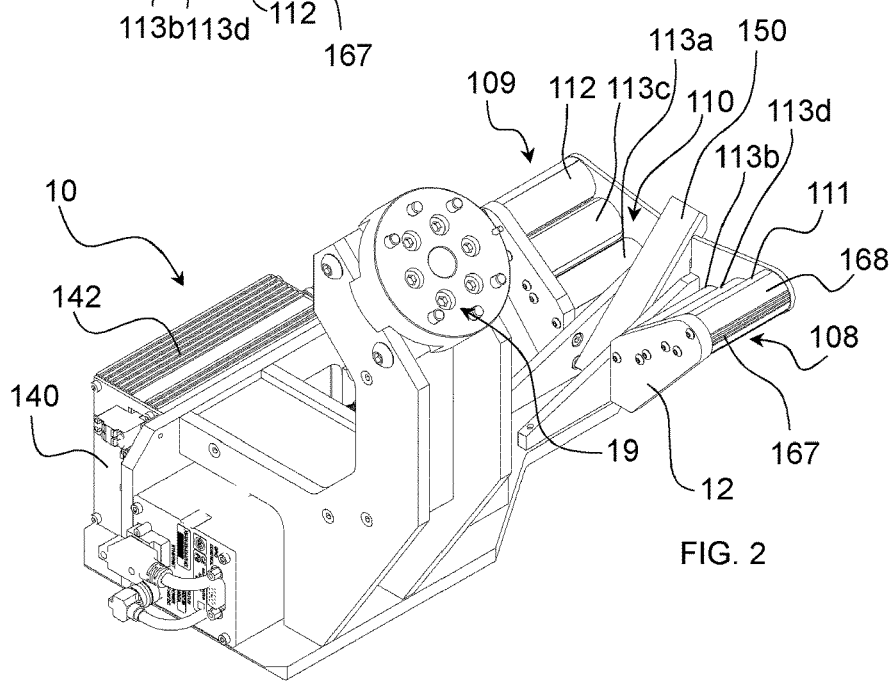
FIG. 2 shows a rear perspective view of the device for checking a tyre of FIG. 1.
Figure 3:
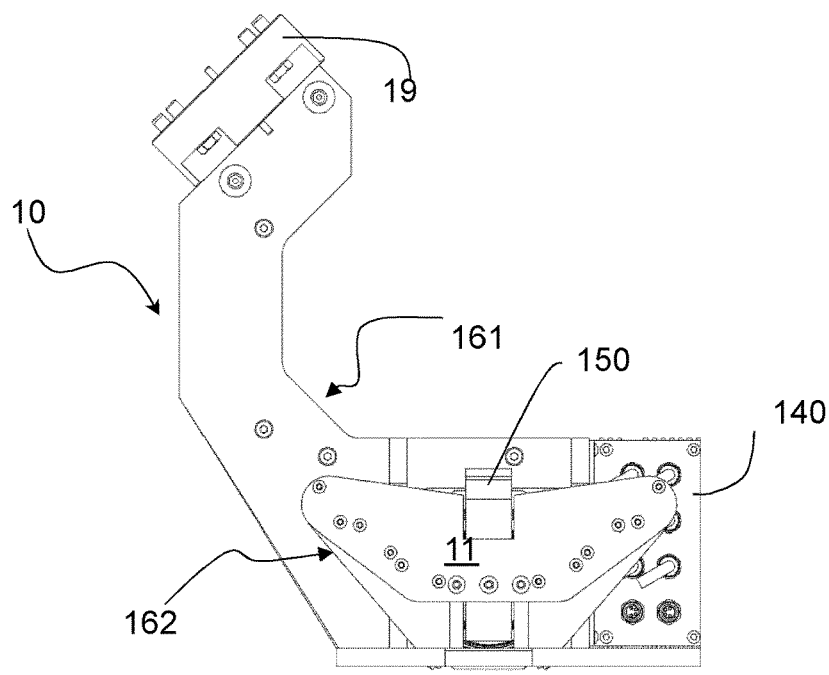
FIG. 3 shows a front view of the device of FIG. 1.
Figure 4:
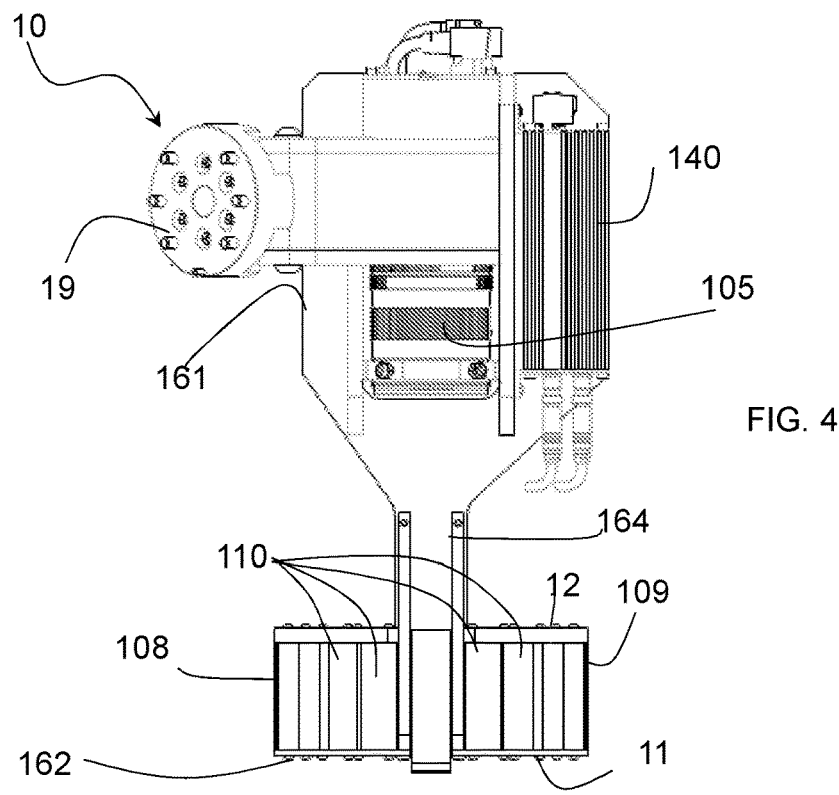
FIG. 4 shows a view from above of the device of FIG. 1.

With particular reference to FIGS. 1 and 2, each light source 110, 108, 109, also includes a support 168, preferably made of aluminium, on which the LED sources 169 are fixed. Preferably, the LED sources 169 are fixed to the respective support 168 through a thermo-conductive paste (not visible in the figures). Advantageously, each support 168 also includes, in an outer surface not in contact with the LED sources 169, a fin arrangement 167 for the dissipation of heat.

Typically, the device 10 comprises a robotized arm 160 (only schematically represented in FIG. 1) on which the first light source 110, the second light source 108 and the third light source 109, as well as the detection system 104 are mounted. The device 10 includes an attachment 19 for fixing to the robotized arm 160. Preferably, the robotized arm 160 is of the anthropomorphous type. Even more preferably, the robotized arm 160 is of the anthropomorphous type with at least five axes.

More in particular, the device 10 comprises a first support 161, to which the linear camera 105 is fixed and a second support 162 to which the first light source 110, the second light source 108 and the third light source 109 are fixed. The first support 161 and the second support 162 are made to form a unit by a connecting arm 164.

The second support 162 comprises two equidistant plates 11 and 12, between which the first light source 110, the second light source 108 and the third light source 109 are arranged. Therefore, each light source or sub-source is connected with a first axial end thereof to the first plate 11 and with a second axial end thereof to the second plate 12. In this way, along the main direction of extension 114, the light sources and/or sub-sources are preferably the same length being substantially confined between two mutually parallel planes.

Preferably, therefore, camera 105 and light sources 110, 108 and 109 form a unit with each other and their relative distance is defined in the mounting step of the device 10 and is kept fixed.

Preferably, the device 10 comprises a drive and control unit 140 configured to selectively activate one or more of said first light source 110, second light source 108 and third light source 109, and to activate the linear camera 105 so as to acquire a respective two-dimensional digital image (in colour or monochromatic) of the linear surface portion, preferably in synchrony with the activation of one or more of said first light source 110, second light source 108 and third light source 109.

Preferably, the drive and control unit 140 is mounted so as to form a unit with the camera 105 and the light sources 110, 108 and 109, in particular it is fixed to the first support 161 of the device 10. Moreover, preferably, the drive and control unit 140 comprises a fin arrangement 142, for greater dissipation of heat.

The device 10 also comprises a reflective element, such as a mirror 150, defining a reflective plane arranged perpendicular to the optical plane 107. The mirror 150 is also arranged between the second light source 108 and the third light source 109, so as to reflect the target line by an angle comprised between about 60° and about 120°.

Preferably, the mirror 150 is divided into two halves by the optical plane 107 that passes through a middle line thereof. Preferably, therefore, the mirror 150 is arranged not only between the second light source and the third light source, but is in between, in spatial position sequence, the second light source 108, the third sub-source 113c, the first sub-source 113a on one side of the optical plane 107, and the second sub-source 113b, the fourth sub-source 113d and the third light source 109 on the other side of the optical plane 107.

The mirror 150 also defines a main direction of extension indicated with 118 in FIG. 6. The main direction of extension is a straight line that belongs to the optical plane 107. This main direction of extension 118 of the mirror 150 is inclined with respect to the main direction of extension 114 of the light sources and/or sub-sources. As stated above, preferably the light sources and the sub-sources have a main direction of extension substantially common to them, being parallel to one another. This common main direction of extension 114 of the light sources and sub-sources preferably forms an angle comprised between 30° and 60° with the main direction of extension 118 of the mirror 150. More preferably, it forms an angle of about 45°.

Moreover, a minimum distance d (again see FIG. 7) between the mirror 150 and the focusing plane 121 of the linear camera 105 (passing through the reflected target line) is less than a minimum distance between any one among the first light source 110, the second light source 108 or the third light source 109 and the focusing plane 121. In FIG. 7, the minimum distances of the light sources and of the sub-sources are equal to the distance of the plane passing through the light sources and the focusing plane 121, since the light sources or the sub-sources are substantially arranged parallel to the focusing plane 121.

Preferably, the length of the mirror L along its main direction of extension 118 is greater than the length ls of any of the light sources or sub-sources along their main direction of extension 114. More preferably, calling the angle formed between the two directions 114 and 118 $\alpha$, gives $L\cos\alpha > ls$.

In this way, as can be seen more clearly from FIGS. 6 and 7, the mirror is the element that extends, at least with respect to the light sources, the closest to the focusing plane 121, in particular with an end thereof 150a, the end along its main direction of extension 118. In other words, the end 150a of the mirror protrudes with respect to the axial ends of the light sources and of the sub-sources in the direction of the focusing plane 121.

Preferably, the mirror 150 includes a reflective layer defining said reflective plane, said reflective layer being an outermost layer of said mirror 150 on which an optical path of a light radiation directed to said camera 105 reflects.

With reference to FIGS. 9 to 12 the operation of the device 10 will now be described in detail.

A first surface portion to be checked (indicated with 212) is selected in the inner surface of the tyre 200. Preferably, but not exclusively, this portion belongs to the shoulder 205, to the bead 206 or corresponds internally to the sidewall 207 of the tyre 200. For example, in FIG. 9, the device 10 is partially inserted inside the tyre 200 and brought closer—through the robotized arm that is not depicted—to a first inner surface portion of the bead 206.

The first light source 110, the second light source 108, and the third light source 109 are driven by the drive and control unit 140 to emit a radiation on the first inner surface portion 212 of the tyre 200. The first source 110 emits diffused radiation on said first surface portion, whereas the second light source 108 and the third light source 109 emit grazing radiation, coming from opposite half-spaces with respect to the optical plane 107, on said first surface portion. Preferably, all three of the light sources emit light radiation to illuminate the first inner surface portion of tyre, for example at a predetermined frequency. The illumination with each light source, however, takes place alternately: in other words for each time period only one among the first light source 110, the second light source 108 or the third light source 109 is switched on, whereas the other two remain switched off. Preferably, the four sub-sources 113a-d of the first light source 110 are switched on together, i.e. in a given time period all four are switched on or all four are switched off. Such a stroboscopic frequency is for example equal to 0.064 ms.

The light coming from the first light source 110, from the second light source 108, or from the third light source 109, is reflected by the first inner surface of the bead 206 of the tyre that has been illuminated and is redirected through the mirror 150 towards the camera 105. The mirror 150 causes a deflection of the trajectory of the light beams by an angle comprised between about 60° and about 120°, more preferably by about 90°.

Preferably, the drive and control unit 140 further controls the camera 105 so as to acquire an image of the first inner surface portion illuminated by the first light source 110, or by the second light source 108, or by the third light source 109, in synchrony with the illumination thereof. Therefore, advantageously, the camera 105 acquires an image of the inner surface portion of tyre 200 illuminated each time the first light source 110 that illuminates the portion with diffused light is switched on, an image of the inner surface portion of tyre 200 illuminated each time the second light source 108 that illuminates the portion with grazing light from one side of the optical plane 107 is switched on and an image of the inner surface portion of tyre 200 illuminated each time the third light source 109 that illuminates the portion with grazing light from the other side of the optical plane 107 is switched on. In this way, advantageously, for each inner surface portion three distinct images to be processed are acquired in which the same portion is illuminated with a radiation having distinct characteristics.

In this way, it is possible to acquire both an image in diffused light and two images in grazing light of the same surface portion. These three images can also form distinct portions of a single two-dimensional image, in which a first portion is obtained with the grazing light, a second portion with grazing light from a first direction of the optical plane (for example from the right) and a third portion with grazing light from a second opposite direction of the optical plane (for example from the left).

The device 10 is also particularly advantageous in the case of measurement with a kit including a deformation element adapted for deforming a surface portion of the tyre that comprises at least in part a linear surface portion to be illuminated and to be acquired. The defects searched for can for example be irregularities on the surface of a tyre (unvulcanised compound, alterations in shape, etc.), structural unevenness, presence of foreign bodies on the surface. Among structural unevenness defects, so-called "carcass creep" are particularly critical, which are rare but potentially very dangerous defects, generated in the interface region between two portions of the tyre having different chemical-physical characteristics, like for example different compounds.

Such defects are in the form of small cuts, typically extending longitudinally, i.e. they follow the circular extension of the tyre, characterised by perfectly matching edges— between which there is no removal or lack of material, this being a characteristic that makes them particularly difficult to identify. The carcass creep can also involve structures of the carcass arranged close to the surface of the tyre, for example close to the inner surface, under the layer of liner typically present. In this case typically the liner itself is involved in the running, also having a laceration at the carcass creep and thus making it possible to identify it through optical inspection.

By suitably deforming a portion of outer wall of a tyre to be checked it is possible to decrease the outer and inner radius of curvature of a deformed surface portion of the tyre, thus highlighting possible defects, in particular carcass creep and other cuts or holes, since the accentuation of the normal external convexity tends to 'open' the edges or perimeters of such defects, making them easier to identify in the subsequent image processing.

The images detected of this adequately compressed surface portion thus have a high quality and/or contain information in number and quality such as to allow a subsequent automatic processing of the latter in order to detect possible defects existing, making the algorithms for automatically detecting defects used for this purpose highly effective.

This type of defect, in order to be properly identified, requires an illumination of relative high power and close to the deformed portion of tyre, i.e. positioning of the checking device very close to the deformation element, otherwise the cut opened by the deformation element "closes" as soon as a distance is reached from the area in which the deformation takes place.

This type of defect, in order to be properly identified, requires an illumination of relative high power and close approach to the deformed portion of tyre, i.e. positioning of the checking device very close to the deformation element, otherwise the cut opened by the deformation element "closes" as soon as it has moved away from the area in which the deformation takes place.

In this case, a deformation element 130 is therefore provided, for example moved by a processing unit (not depicted), which goes into contact with the tyre, preferably at the outer wall thereof 204, so as to preferably apply a force against it and deform a portion of the aforementioned outer wall 204.

Preferably, the deformation element 130 comprises a compression member 131 and a positioning actuator 132 adapted for moving the compression member along the direction of the compression force. As an example, the positioning actuator 132 can be a pneumatic cylinder. Therefore, the compression member can be brought into contact with or away from the tyre 200. Preferably, the compression member 131 comprises a thrusting roller.

Figure 10:
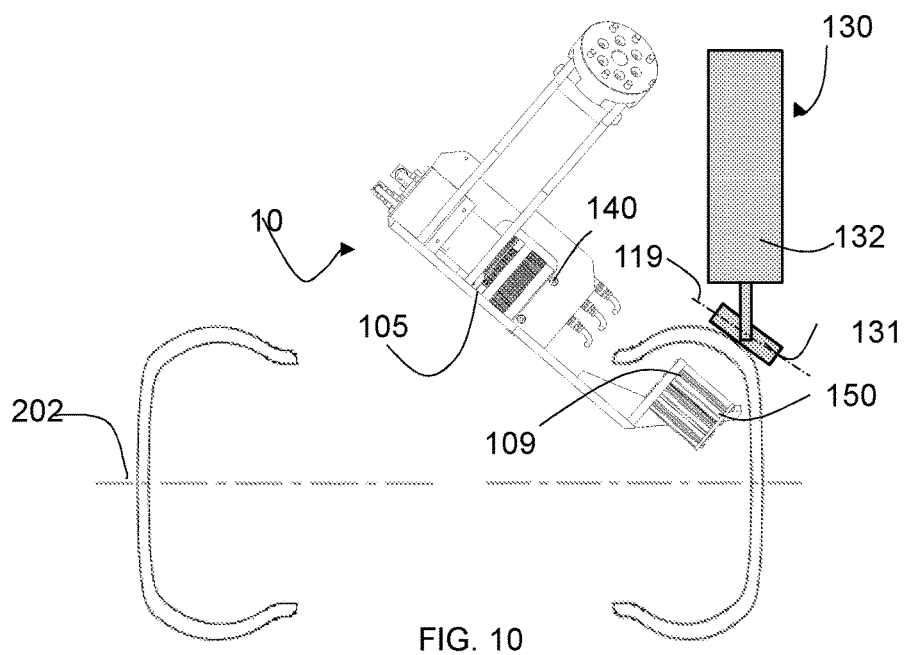
Figure 11:
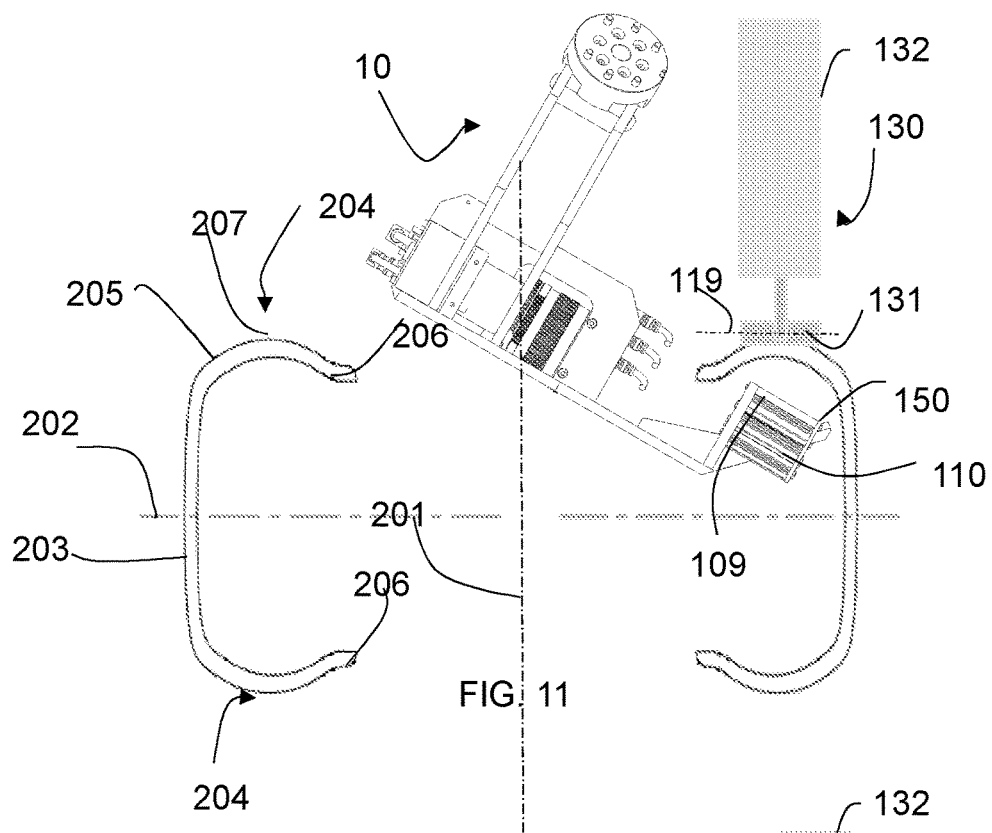
Figure 12:
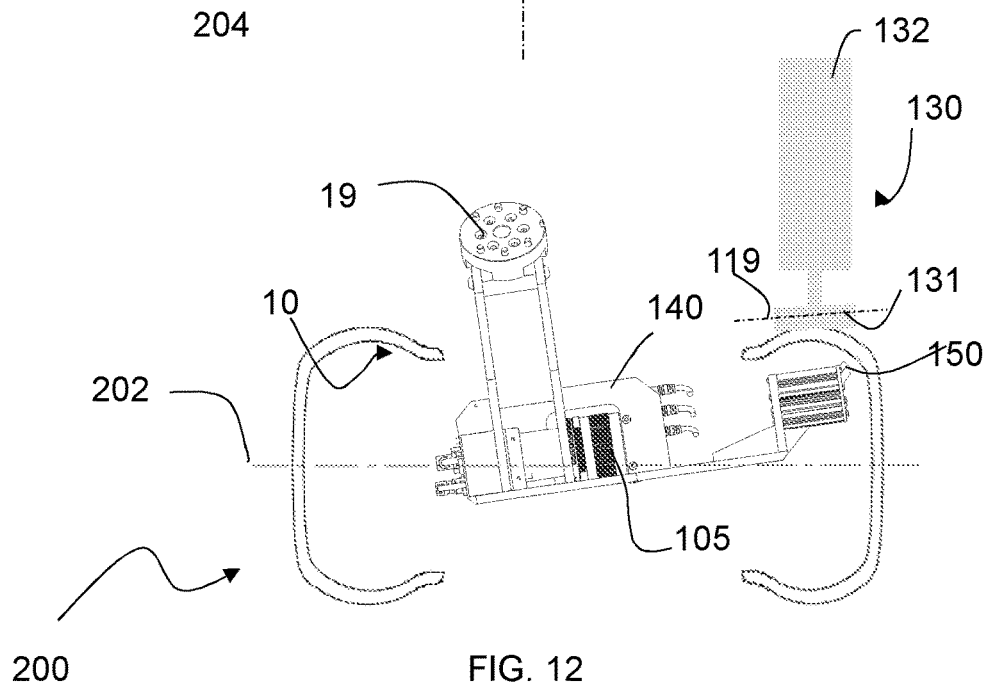

Preferably, the thrusting roller can be rotated about a rotation axis thereof, indicated with 119 in FIGS. 10, 11 and 12. The axis 119 of the thrusting roller always lies on a plane passing through the axis 201 of the tyre 200 and through the radial direction of the outer wall portion subjected to deformation. Preferably, the axis 119 of the compression roller, in the absence of forces, in other words in rest position, is perpendicular to the axis of the tyre. The axis of the roller, in operation, can differ from such a perpendicular condition with the axis of the tyre (as for example shown in FIG. 10) for example within a measurement of 30° from the perpendicular condition.

Preferably, the deformation element 130 comprises a radial movement member (not shown, for example a further electric motor and a system of guides and sliding blocks to guide the radial movement) adapted for moving the deformation member and the positioning actuator as a unit along the radial direction of the tyre. Therefore, the deformation element can be moved away from the tyre when not in use.

Preferably, the deformation element 130 is adapted for elastically deforming a portion of an outer wall 204 of the tyre 200, applying a compression force on an outer contact surface belonging to the outer wall portion, pressing the aforementioned thrusting roller on the outer contact surface. The position of the roller, the force applied or the movement imposed on the outer contact surface along a rotation axis of the tyre is predetermined and depends on the type of tyre to be checked. The tyres 200 can have a different elasticity and deformability according to the type and model, and therefore the force applied or the deformation imposed by the deformation element 130 is preferably dependent on the type of tyre 200 to be checked. The deformation involves both the inner surface and the outer surface of the tyre 200.

According to the invention therefore, having selected a surface portion of the tyre to be deformed, the device 10 is brought towards the consequent deformed portion of inner surface as can be seen in FIG. 10. Preferably, as represented in FIG. 10, the inner deformed portion to be checked is a portion of the shoulder 205 of the tyre 200.

Preferably, the entire remaining portion of the outer wall 204, i.e. of the shoulder 205, of the tyre 200 remains undeformed. As an example, the compression force is such as to deform the portion of outer wall 204 so that the maximum excursion, taken between all of the points of said portion of outer wall, between the position in the absence of forces and the deformed position, the excursion being taken along the direction of the compression force, is equal to a value comprised between about 20 and about −20 mm.

A processing unit drives the robotized arm 160 to bring the light sources 110, 108, 109 towards the surface of the tyre 200, so that an inner linear surface portion inside the first deformed portion at least partially coincides with, or is close to, the target line in the focusing plane 121.

The detection of an image of the inner surface portion of shoulder 205 through the light sources and the camera takes place in an analogous manner to what is described above with reference to the bead, and therefore the three light sources 110, 108, 109 are switched on alternately and for each distinct illumination a linear image is acquired through the linear camera 105.

Optionally, two more portions of the surface of the tyre are selected, preferably but not necessarily again belonging to the outer wall 204 of the outer surface thereof, where a deformation and consequent check of the corresponding deformed inner surfaces is to be carried out. The positioning of the device 10 for checking these two further portions is represented in FIGS. 11 and 12. Both of the portions of inner surface checked in FIGS. 11 and 12 axially correspond to the sidewall 207 of the tyre 200. The examination of these surface portions, in particular for large sized tyres, can like in this case require the movement of the device in two distinct positions so as to be able to illuminate the entire inner surface axially corresponding to the sidewall, which would not be able to be detected through illumination and acquisition of images in a single position. The deformation element 130 can thus be positioned, preferably again through the processing unit of the apparatus, at two distinct surface portions of the tyre 200, so as to deform a second and a third surface portion of the tyre. In this way, two new measurements can be made, bringing the device 10 closer into the new positions so as to obtain an illumination of the further deformed inner surface portions of the tyre. See for example the difference between the position of the deformation element 130 in FIGS. 10, 11 and 12 and the consequent different position of the device 10 in the three figures. Moreover, in FIG. 10, the rotation axis 119 of the thrusting roller, positioned at the shoulder 205, is inclined with respect to the plane defined by the support of the tyre 200, whereas in FIGS. 11 and 12 the rotation axis 119 of the thrusting roller is substantially perpendicular to the rotation axis 201 of the tyre 200.

The illumination and the acquisition of the images through the light sources 110, 108 and 109 and the linear camera 105 takes place according to what is described with reference to FIGS. 9 and 10.

Advantageously, in each of the positions represented in FIGS. 9-12, the support 102 on which the tyre is positioned (see FIG. 5) is set in rotation during the check of the tyre itself. As stated above, the drive and control unit 140 preferably controls the camera 105 so as to acquire an image of the inner surface portion illuminated by the first light source 110 or by the second light source 108 or by the third light source 109 in synchrony with the activation thereof.

Preferably, the apparatus comprises an encoder (not shown) for detecting the angular position of the support, the drive and control unit being configured to activate said first light source, second light source, and preferably third light source and drive the detection system as a function of an angular position signal of the support sent by the encoder.

However, since the tyre is preferably in rotation while these three distinct images are acquired, they are not exactly the image of the same inner linear surface portion of tyre, since the latter is rotated during the switching on and off of the light sources.

As an example, the time difference between the acquisition of the first linear image and of the second linear image, as well as between the second linear image and the third linear image and then cyclically between the first linear image and the third linear image, is less than 0.2 milliseconds. Therefore, in this very limited time period, the movement is "relatively small" and therefore it is still possible to state that, for substantially the same surface portion three linear images are obtained, each with a different illumination.

The expression "substantially the same surface portion" means that the first light source, the second light source and the third light source illuminate three respective surface portions that can be spatially offset from one another but are comparable according to the present invention, i.e. they show the same elements substantially in the same position. For example, the three surfaces can be offset, on the plane of the surface itself, by a distance of less than 0.2 mm, preferably less than, or equal to, 0.1 mm. Advantageously, said distance is less than, or equal to, the linear surface dimension associated with a pixel (the latter as an example being equal to 0.1 mm), in the case in which the detection system includes a camera, for example a matrix or linear camera. In other words each pixel of the first image shows a micro-surface portion that is less than 0.2 mm away from the micro-surface portion shown by the pixel of the second image corresponding to each said pixel.

In other words, the three images can be substantially juxtaposed pixel by pixel, although the real linear surface portion associated with a single linear image does not exactly coincide for the three images, due to the rotation of the tyre that has occurred in the meantime. However, the choice of the acquisition frequency of the images and of the rotation speed is such that the three images are interlaced and thus comparable pixel by pixel. Advantageously each pixel of the first (or second or third) image shows a surface micro-portion that differs from the surface micro-portion shown by the pixel of the second (or respectively third or first) image corresponding to said each pixel apart from the linear surface dimension associated with a pixel, as an example the spatial divergence being equal to about one third of a pixel. In this way, the three images are interlaced with each other and the acquisition of the three linear images takes place in a time period during which the tyre has rotated by a portion equal to one pixel (as an example equal to about 0.1 mm).

Once the desired rotation of the tyre has been carried out to examine the desired surface portion, preferably at least one complete rotation to acquire the entire circular extension, a single digital image is obtained that is made with all of the digital images of the sequence of linear portions each illuminated with a respective light source. The processing unit receives such an image from the detection system and extracts the corresponding first image, second image and third image of the entire desired surface portion therefrom.

In the case in which a single image is acquired as described above formed from a portion with diffused light [A], a portion with grazing light dx [B] and a portion with grazing sx [C], a succession repeated until the entire tyre is acquired, an overall image is obtained formed by the sequence ABCABCABCABCABCABCABCABCABC . . . In processing this image is divided into three effective images, obtaining AAAAAAAA . . . BBBBBBBB . . . CCCCCCCC . . .

Preferably, the processing unit is also configured for the following functions: receiving the images acquired from the linear camera; and processing the images in order to check the surface portion. The processing unit comprises for example a PC or a server. Preferably, the processing unit is adapted for processing the second image and the third image to be processed obtained with grazing light by comparing them in order to obtain information on an altimetric profile of the surface portion. Preferably, the comparison between the second image and the third image to be processed comprises calculating a difference image in which each pixel is associated with a value representative of the difference between the values associated with the corresponding pixels in the second image and in the third image to be processed.

Preferably, before comparing the second image and the third image to be processed it is foreseen to equalise the second image and the third image to be processed, for example equalising the average luminosity thereof globally or locally.

Preferably, the processing unit processes the first image to be processed in diffused light to detect the possible presence of defects on the surface portion, using the information obtained by the aforementioned comparison between the second image and the third image to be processed.

Preferably the processing unit is configured to calculate the difference between the second image and the third image in order to obtain information on an altimetric profile (e.g. possible presence or absence of projections and/or depressions) of the linear surface portion.

Preferably, calculating the difference between the second image and the third image comprises calculating a difference image in which each pixel is associated with a value representative of the difference between the values associated with the corresponding pixels in the second image and in the third image. In this way, it is possible to use the image obtained by the difference between the second image and the third image to highlight the three-dimensional elements (such as raised pitting on the outer surface of the tyre or raised writing) and to take into account such information in the processing of the image in diffused light to look for defects.

The invention claimed is:

1. A device for checking a tyre in a tyre production line, comprising:
   a detection system comprising a camera in which a target optical line lying on an optical plane passing through said camera is defined;
   a first light source, a second light source and a third light source, said second light source and said third light source being arranged at opposite sides with respect to said optical plane and symmetrically with respect to said first light source, said first light source being adapted for emitting a first diffused light radiation on a surface portion of said tyre coinciding with or close to said target optical line, said second light source and third light source being adapted for emitting a second grazing light radiation and a third grazing light radiation on said surface portion of said tyre; and
   a reflective element defining a reflective plane arranged perpendicular to said optical plane, said reflective element being arranged between said second light source and third light source, said reflective element being adapted for reflecting said target optical line by an angle comprised between about 60° and about 120° and wherein a minimum distance between said reflective plane and a focusing plane of said camera passing through said reflected target optical line is smaller than a minimum distance between one of said first light source, second light source and third light source and said focusing plane.

2. The device according to claim 1, wherein said minimum distance between said reflective plane and said focusing plane of said camera passing through said reflected target optical line is smaller than each minimum distance between said first light source, second light source and third light source and said focusing plane.

3. The device according to claim 2, wherein said first light source includes a first light sub-source and a second light sub-source, said first light sub-source and said second light sub-source being arranged symmetrically with respect to said optical plane.

4. The device according to claim 3, wherein said second light source and said third light source each comprise a single light sub-source.

5. The device according to claim 4, wherein said first light sub-source and said second light sub-source of said first light source are coplanar and define a plane substantially parallel to the focusing plane.

6. The device according to claim 5, wherein a distance between said focusing plane and a plane passing through said first light sub-source and said second light sub-source is comprised between about 85 mm and about 95 mm.

7. The device according to claim 6, wherein said first light source includes a third light sub-source and a fourth light sub-source, said third light sub-source and said fourth light sub-source being arranged symmetrically with respect to said optical plane.

8. The device according to claim 7, wherein said third light sub-source and said fourth light sub-source are coplanar and define a plane substantially parallel to the focusing plane.

9. The device according to claim 8, wherein a distance between said focusing plane and a plane passing through said third light sub-source and said fourth light sub-source is comprised between about 75 mm and about 85 mm.

10. The device according to claim 9, wherein a distance between said first light source and said focusing plane is greater than a distance between said second light source and said focusing plane or between said third light source and said focusing plane.

11. The device according to claim 10, wherein said second light source and said third light source are coplanar and define a plane substantially parallel to the focusing plane.

12. The device according to claim 11, wherein a distance between a plane parallel to said focusing plane and passing through a light sub-source of said first light source and a plane parallel to said focusing plane and passing through said second light source and said third light source is comprised between about 10 mm and about 40 mm.

13. The device according to claim 12, wherein one or more of i) said first, second, third and fourth light sub-sources of said first light source, ii) said single light sub-source of said second light source or iii) said single light sub-source of said third light source extend along a respective main direction of extension substantially parallel to said optical plane.

14. The device according to claim 13, wherein all of the light sub-sources of said first light source, of said second light source and of said third light source each extend along a main direction of extension substantially parallel to said optical plane.

15. The device according to claim 14, wherein said reflective element extends along a main direction of extension in said optical plane.

16. The device according to claim 15, wherein at least one of said light sub-sources and said reflective element has a substantially rectilinear configuration along its respective main direction of extension.

17. The device according to claim 16, wherein a length along the main direction of extension of said reflective element is greater than a length along the main direction of extension of one of: said first light sub-source, said second light sub-source, said third light sub-source, said fourth light sub-source of said first light source, said second light source or said third light source.

18. The device according to claim 17, wherein
the length of i) one among: said first light sub-source, said second light sub-source, said third light sub-source and said fourth light sub-source of said first light source and of ii) said second light source, or
the length of i) one among: said first light sub-source, said second light sub-source, said third light sub-source and said fourth light sub-source of said first light source and of ii) said third light source,
is substantially the same.

19. The device according to claim 18, wherein said second light source and said third light source are arranged symmetrically with respect to said optical plane.

20. The device according to claim 19, comprising a drive and control unit configured to:
selectively activate at least one among said first light source, second light source and third light source, and
activate said camera to acquire a respective two-dimensional image of said surface portion in synchrony with the activation of said at least one among said first light source, second light source and third light source.

21. The device according to claim 20, wherein said drive and control unit is adapted for controlling said detection system to acquire three distinct images, each image corresponding to the switching on of a different light source among said first light source, said second light source and said third light source.

22. The device according to claim 21, wherein said reflective element is adapted for reflecting said target optical line by an angle of about 90°.

23. The device according to claim 22, wherein said reflective element includes a reflective layer defining said reflective plane, said reflective layer being an outermost layer of said reflective element on which an optical path of a light radiation directed to said camera reflects.

24. The device according to claim 23, including a first support to which said camera is fixed.

25. The device according to claim 24, wherein said drive and control unit is fixed to said first support.

26. The device according to claim 25, including a second support to which said first light source, said second light source and said third light source and said reflective element are fixed.

27. The device according to claim 26, wherein said first support and said second support are connected and made integral with one another by a connecting arm.

28. The device according to claim 27, wherein said second support comprises two equidistant plates between which said first light source, said second light source and said third light source are arranged.

29. The device according to claim 28, wherein one of said first light source, said second light source or said third light source includes a converging lens adapted for restricting an emission field angle of a respective one of said first light radiation, said second light radiation or said third light radiation to a value comprised between about 15° and about 45°.

30. The device according to claim 29, wherein said first light source, said second light source or said third light source includes one or more light emitting diodes.

31. The device according to claim 30, where a respective angle formed between said focusing plane and any plane passing through said target optical line and any point, respectively, of said second light source or third light source is less than or equal to 60°.

32. The device according to claim 31, wherein said surface portion belongs to a portion of a shoulder surface of said tyre.

33. The device according to claim 32, wherein said surface portion corresponds, inside the tyre, to a surface portion of a sidewall of said tyre.

34. The device according to claim 33, wherein said surface portion belongs to a bead surface portion of said tyre.

35. The device according to claim 34, wherein said camera is a linear camera and said surface portion is a linear surface portion.

36. A kit for checking a tyre, the kit comprising:
the device according to claim 1; and
a deformation element configured to form an elastically deformed portion on said tyre through physical contact.

37. The kit according to claim 36, wherein said deformed surface at least partially includes said surface portion.

38. The kit according to claim 37, wherein a distance between said first light source and said surface deformed by said deformation element is comprised between about 85 mm and about 95 mm.

* * * * *